United States Patent [19]
Kensicher et al.

[11] Patent Number: 5,880,085
[45] Date of Patent: Mar. 9, 1999

[54] AGENT WHICH IS COMPATIBLE WITH SURFACTANTS WHICH ARE USED IN DETERGENTS AND COSMETICS

[75] Inventors: Yves Kensicher, Lozanne; Jean-Marc Suau, Lucenay, both of France

[73] Assignee: Coatex S.A., Genay, France

[21] Appl. No.: 917,570

[22] Filed: Aug. 26, 1997

[30] Foreign Application Priority Data

Aug. 26, 1996 [FR] France .................................. 96 10585

[51] Int. Cl.$^6$ ..................................................... C11D 3/37
[52] U.S. Cl. ............................................................ 510/476
[58] Field of Search .................................. 510/108, 119, 510/123, 124, 476

[56] References Cited

FOREIGN PATENT DOCUMENTS

| | | |
|---|---|---|
| 458599 A2 | 11/1991 | European Pat. Off. . |
| 0 577 525 | 1/1994 | European Pat. Off. . |
| 47-39206 | 10/1972 | Japan . |
| 59-135293 | 8/1984 | Japan . |
| 2 027 045 | 2/1980 | United Kingdom . |
| 2 104 091 | 3/1983 | United Kingdom . |
| 91/06623 | 5/1991 | WIPO . |
| WO 91/06623 | 5/1991 | WIPO . |
| 91/09067 | 6/1991 | WIPO . |

*Primary Examiner*—Paul Lieberman
*Assistant Examiner*—John R. Hardee
*Attorney, Agent, or Firm*—Oblon, Spivak, McClelland, Maier & Neustadt, P.C.

[57] ABSTRACT

The use of copolymers to obtain detergent or cosmetic compositions which are stable to phase separation, where the copolymers have the general formula:

$$(X)_a—(Y)_b—(Z)_c$$

in which
- X is an anionic monomer unit;
- Y is a nonionic monomer unit; and
- Z is a cationic monomer unit;
- a is the weight percentage of X in the copolymer, based on the total weight of all monomers, and is 95 to 15 wt. %;
- b is the weight percentage of Y in the copolymer, based on the total weight of all monomers, and is 0 to 65 wt. %; and
- c is the weight percentage of Z in the copolymer, based on the total weight of all monomers, and is 5 to 60 wt. %.

19 Claims, No Drawings

AGENT WHICH IS COMPATIBLE WITH SURFACTANTS WHICH ARE USED IN DETERGENTS AND COSMETICS

BACKGROUND OF THE INVENTION

1. Field of the Invention

The present invention relates to a method of stabilizing compositions containing surfactants by adding a copolymer to the composition, where the copolymer contains anionic monomer units, cationic monomer units having a side chain containing a surface-active group and, optionally, nonionic monomer units and additional cationic monomer units which do not contain a surface-active group. The copolymer may be used, for example, to stabilize detergent and cosmetic compositions containing surfactants against phase separation.

2. Description of the Background

Modern detergents and cosmetics tend increasingly to contain rheological modifiers and/or anti-tartar agents (in the case of dentifrices and the like), surfactants (anionic, cationic, amphoteric or nonionic), and also, in many cases, "builders" (such as borates, citrates, sodium formate and salts of weak acids), along with, possibly, a variety of other agents (e.g. propylene glycol, optical brighteners, etc.).

Those skilled in the art are therefore confronted with the problem of the compatibility of a rheological modifier (e.g. dispersant or thickener) and/or an anti-tartar agent with the surfactants present in the formulation. Heretofore, lacking a solution to this compatibility problem, those skilled in the art have had to choose dispersants, thickeners or anti-tartar agents based on the surfactant(s) used in the detergent or cosmetic formulation.

SUMMARY OF THE INVENTION

It is an object of the present invention to provide a method of stabilizing compositions containing surfactants.

It is another object to provide compositions which contain surfactants and are stable against phase separation.

It has been discovered, surprisingly, in connection with the present invention, that the use of certain amphoteric polymers enables flexible formulation of detergent and cosmetic compositions without sacrificing compatibility between the components. Detergent and cosmetic formulations may be formulated which are stable and do not separate into two phases, regardless of the types of surfactants, rheological modifiers, and/or anti-tartar agents present.

The amphoteric polymers of the present invention are comprised of at least two monomer groups ("motifs"), each of which comprises one or more monomer units. The first monomer group is comprised of one or more ethylenic anionic monomer units which contain at least one negatively charged group. The second monomer group is comprised of one or more ethylenic cationic monomer units, where at least one of the cationically charged monomer units has a surface-active structure; i.e., is comprised of one or more side chains consisting of alkyl groups, aryl groups, alkylaryl groups, or aralkyl groups having at least 8 carbon atoms, in which the cationic charge is separated from the polymer skeleton by a chain having three or more oxyethylene groups, e.g., —OCH$_2$CH$_2$—. The copolymer may, optionally, contain a third monomer group ("motif"), comprised of one or more nonionic monomer units.

Thus the present inventors have solved the problem of selecting rheological modifiers (e.g., dispersants or thickeners), and/or selecting anti-tartar agents, for a given surfactant or surfactant mixture, such that it is no longer necessary to take the surfactant(s) into account when choosing a rheological modifier.

The objects described above, and others, are accomplished by the use of specific copolymers to obtain detergent or cosmetic compositions which are stable regardless of the surfactant(s) present and, in particular, regardless of the nature of the charge (anionic, cationic, amphoteric or nonionic) of the surfactants. The copolymers have general formula:

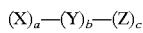

where

X represents the anionic monomer group ("motif") comprised of one or more ethylenic monomers having a negative charge;

Y represents the optional nonionic monomer group ("motif") comprised of one or more ethylenic nonionic monomers;

Z represents the cationic monomer group ("motif") comprised of one or more ethylenic monomer units having a positive charge, where at least one of the monomer units has a surface-active structure; i.e., is comprised of one or more side chains consisting of alkyl groups, aryl groups, alkaryl groups, or aralkyl groups having at least 8 carbon atoms;

a represents the percent by weight of X in the copolymer, based on the total weight of all monomers, and is from 95 to 15 wt. % (all ranges in this description include the end points unless specified otherwise), preferably 80 to 25 wt. %;

b represents the percent by weight of Y in the copolymer, based on the total weight of all monomers, and is from 0 to 65 wt. %, preferably 20 to 50 wt. %; and c represents the percent by weight of Z in the copolymer, based on the total weight of all monomers, and is from 5 to 60 wt. %, preferably 10 to 35 wt. %.

The objects of the invention may also be accomplished with a composition containing one or more surfactants and at least one of the copolymers described above. This composition may contain other rheological modifiers, in addition to the copolymer described above.

A more complete appreciation of the invention and many of the attendant advantages thereof will be readily obtained as the same becomes better understood by reference to the following detailed description.

DETAILED DESCRIPTION OF THE INVENTION

The copolymers of the present invention are always comprised of at least two monomer groups ("motifs"), the first of which is comprised of one or more ethylenic monomer units having an anionic charge, and the second of which is comprised of one or more ethylenic monomer units having a cationic charge and having a surface-active structure, i.e., the monomer unit contains one or more side chains containing at least one alkyl group, aryl group, alkaryl group, or aralkyl group and having at least 8 carbon atoms. The copolymers used according to the invention may also be comprised of a third, optional, group ("motif") comprised of one or more nonionic units.

In a preferred embodiment, the copolymers have the general formula (I):

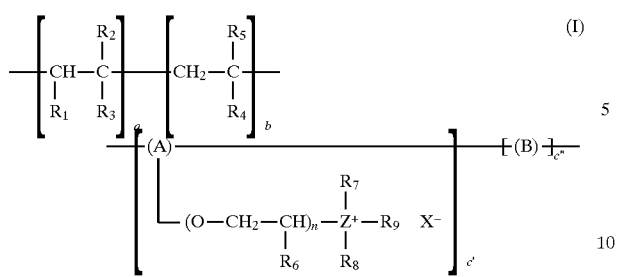 (I)

where
1. In the anionic monomer units:
   $R_1$ is H or COOH (which may be completely or partially neutralized, i.e., COOM, where M is a metal ion, such as an alkali metal ion (e.g., $Na^+$ and $K^+$) or an ammonium ion (e.g., $NH_4^+$);
   $R_2$ is H or $CH_3$;
   $R_3$ is a group having at least one acid function, which may be completely or partially neutralized, for example COOH or COOM, where M is a metal ion, such as an alkali metal ion (e.g., $Na^+$ and $K^+$) organ ammonium ion (e.g., $NH_4^+$); and
   a is the percent by weight of the anionic monomer units in the copolymer, based on the total weight of all monomers, and is 95 to 15 wt. %, inclusive of all specific values and subranges therebetween, preferably 80 to 25 wt. %;
2. In the optional nonionic monomer units:
   $R_4$ is
   —CO—$NH_2$, —CO—$OR_4'$, —CO—$NR_4''R_4'''$, or

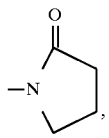

in which
   $R_4'$ is an alkyl or alkoxy group having 1 to 4 carbon atoms;
   $R_4''$ is H or an alkyl group having 1 to 4 carbon atoms;
   $R4'''$ is an alkyl group having 1 to 4 carbon atoms;
   $R_5$ is H or $CH_3$; and
   b is the percent by weight of the nonionic monomer units in the copolymer, based on the total weight of all monomers, and is 0 to 65 wt. %, inclusive of all specific values and subranges therebewteen, preferably 20 to 50 wt. %;
3. In the cationic monomer units having a surface-active group:
   A is a unit derived from a polymerizable unsaturated, preferably ethylenically unsaturated, radical selected from the group consisting of (meth)acrylate esters, maleate esters (or hemiesters), itaconate esters (or hemiesters), crotonate esters, vinylphthalate esters (or hemiesters), an unsaturated urethane (e.g. (meth) acrylic urethane, α,α-dimethyl-m-isopropenylbenzyl urethane, and allylurethane), allylic ethers, substituted or unsubstituted (meth)acrylamides, and vinylic groups;
   $R_6$ is H or $CH_3$;
   n is 3 to 30;
   $R_7$ is an alkyl group having 1 to 4 carbon atoms;

Z is N or S;
   X is a sulfate or halide counterion;
      where, when Z is N:
      $R_8$ is an alkyl group having 8 to 22 carbon atoms, or a group having the formula:

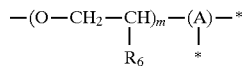

in which
         A has the same meaning as above and each bond from A marked by an * is connected to a monomer unit in another polymer chain (backbone) of formula (I), and
         m is 3 to 30,
         $R_6$ is as described above; and
   $R_9$ is an alkyl group having 8 to 22 carbon atoms;
      and, when Z is S:
      $R_8$ does not exist; and
      $R_9$ is an alkyl group having 8 to 22 carbon atoms; and
   c' is the percent by weight of the monomer units having a cationic charge and a surface-active structure in the copolymer, based on the total weight of all monomers, and is 5 to 60 wt. %, inclusive of all specific values and subranges therebetween, preferably 10 to 35 wt. %; and
4. In the optional cationic monomer units which do not contain a surface-active group:
   B is a cationic monomer unit which does not contain a surface-active group and is derived from a monomer selected from the group consisting of trimethylammoniumethyl (meth)acrylate chloride and/or trimethylammoniumethyl (meth)acrylate sulfate, and N-(N',N', N'-trimethylammonium)propyl(meth)acrylamide chloride and/or N-(N',N',N'-trimethylammonium)propyl (meth)acrylamide sulfate; and
   c" is the percent by weight, based on the total weight of the monomers, of the monomer units having a cationic charge but not having a surface-active structure, and is 0 to 55 wt. %, inclusive of all specific values and subranges therebetween; and
   c'+c"=c, where c is the total percent by weight of all the cationic monomers in the copolymer, and is 5 to 60 wt. %, preferably 10 to 35 wt. %.

As used herein, the term (meth)acrylic means acrylic and methacrylic. Similarly, meth(acrylate) refers to acrylate and methacrylate, etc. Unless otherwise specified all of the carbon number ranges described above include all specific values and subranges therebetween. Unless otherwise specified, alkyl groups may have any structure, e.g., linear, branched or cyclic.

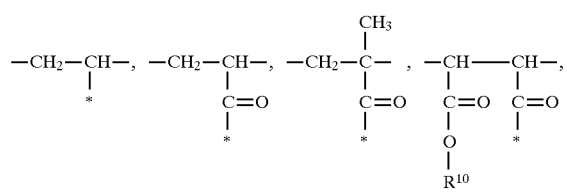

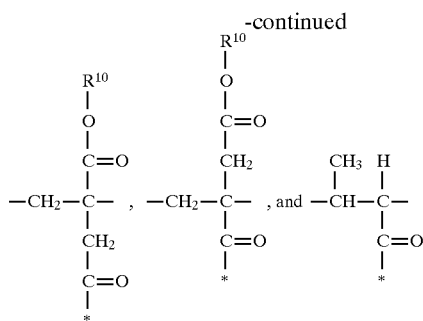

where the bonds marked with an * link A to the surface-active side chain group containing Z. Each bond which is not marked with an * is connected to another monomer unit in the backbone of the copolymer. $R^{10}$ is H or a $C_{1-4}$ alkyl group.

The copolymers may be prepared by conventional synthetic methods, including radical copolymerization solution processes, direct or reverse emulsion polymerization, suspension or precipitation processes; with suitable initiators and regulators. The polymerization may be conducted in any suitable media, such as an aqueous, alcoholic, aqueous-alcoholic, aromatic or aliphatic medium, or in a halogenated solvent. The polymerization is conducted with at least two of the monomer groups ("motifs") as described above, i.e., at least one monomer from the anionic and at least one monomer from the cationic group.

Thus, the copolymerization medium may contain water, methanol, propanol, isopropanol, one or more butanols, dimethylformamide, dimethylsulfoxide, tetrahydrofuran, acetone, methyl ethyl ketone, ethyl acetate, butyl acetate, hexane, heptane, benzene, toluene, ethylbenzene, xylene, one or more halogenated solvents (e.g. tetrachloromethane, trichloromethane, dichloromethane, one or more ethers of monopropylene glycol, or diethylene glycol. Mixtures of these solvents may be used as well.

The copolymers for use according to the invention are preferably those having a specific viscosity, $\mu$, of 0.3 to 10, inclusive of all specific values and subranges therebetween, including 0.4, 0.5, 0.6, 0.7, 0.8, 0.9, 1, 2, 3, 4, 5, 6, 7, 8 and 9. The specific viscosity of the copolymers is determined by the following method. First, a solution of the sodium salt of the copolymer in water is prepared by dissolving 50 g of the dry copolymer in 1 L of a distilled water solution containing 60 g of sodium chloride. Then, using a capillary viscometer placed in a bath maintained at 25° C. by a thermostat, the following measurements are made:

1. the efflux time of a given volume of the solution containing the sodium salt of the copolymer, and
2. the efflux time of the same volume of the corresponding aqueous sodium chloride solution which does not contain the copolymer.

The specific viscosity, $\mu$, is defined as:

$$\mu = (t_{copolymer} - t_{NaCl})/t_{NaCl}$$

where $t_{copolymer}$ is the efflux time of the copolymer solution, and $t_{NaCl}$ is the efflux time of the NaCl solution.

The capillary tube is preferably chosen so that the efflux time of the NaCl solution without the copolymer is about 90 to 100 sec, which provides high precision in measuring the specific viscosity of the copolymer.

After the polymerization, the acid copolymers in aqueous solution are recovered, and according to the invention, they may be used as recovered. Optionally, a neutralizing agent may be used in the formulation. The selected copolymers in an aqueous solution may be neutralized, completely or partially, by the neutralizing agent. Preferably the neutralizing agent has a monovalent function, e.g., an alkaline cation. Suitable neutralizing agents include alkali metal hydroxides, e.g., NaOH and KOH.

In practice, the liquid or heterogeneous phase resulting from the copolymerization and containing the acid copolymer selected may be used in a neutralized form as a rheological modifier and/or anti-tartar agent; or this phase may be dried by known means to eliminate the liquid phase and isolate the copolymer as a fine powder which may be used in this form.

Examples of anionic surfactants which may be present in anionic formulations are: alkylbenzenesulfonates (e.g. tetrapropylenebenzenesulfonate), alkylsulfonates, alkyl sulfates, alkyl ether sulfates, and others. These surfactants may have 8 to 30 carbon atoms, inclusive of all specific values and subranges therebetween.

Examples of cationic surfactants which may be present in cationic formulations are, for example, imidazoline salts, dialkyldimethylammonium chlorides, and alkyldimethylbenzylammonium chlorides. These compounds may have 8 to 30 carbon atoms, inclusive of all specific values and subranges therebetween.

Nonionic surfactants for all types of formulations may be chosen from among, e.g., ethoxylates of fatty alcohols, oxo alcohols, alkylphenols, alkyl polyglycol ethers, alkylphenol polyglycol ethers, alkanolamides of fatty acids, etc. These compounds may have at least 8 carbon atoms, preferably 8 to 50 carbon atoms, inclusive of all specific values and subranges therebetween.

Many specific examples of anionic, cationic and nonionic surfactants that may be used in the present invention are provided by *International Cosmetic Ingredient Handbook*, The Cosmetic, Toiletry, and Fragrance Association (CTFA), third edition, 1995, pp. 913–929, incorporated herein by reference.

The copolymer may be used to stabilize a composition containing at least one surfactant, by combining the copolymer and the composition. More than one copolymer may be used. The composition is preferably a detergent or cosmetic composition. Liquid compositions are preferred. In a particularly preferred embodiment, the composition contains water, i.e., the composition is aqueous. The composition may contain 0.01 to 50% by weight of the surfactant, inclusive of all specific values and subranges therebetween. The weight percent range for the surfactant is based on the dry weight of the surfactant. The amount of copolymer added to the composition may be 0.01 to 15% by weight, preferably 0.1 to 10%, more preferably 0.2 to 8% and most preferably 0.25 to 5% by weight, based on the weight of the composition. It is particularly preferred to use at least 0.25 wt. % of the copolymer. These weight percent ranges are based on the dry weight of the copolymer, and include all specific values and subranges therebetween.

In a preferred embodiment, the weight ratio of copolymer to surfactant in the stabilized composition may be 0.01 to 20, preferably 0.05 to 10, more preferably 0.08 to 5 and, most preferably, 0.1 to 2. These weight ratio ranges include all specific values and subranges therebetween, including 0.02, 0.2, 0.5, 1, 2, 8, 12, 15 and 18.

When the composition is aqueous, the amount of water may be 1 to 99 wt. %, based on the total weight of the composition. This range includes all specific values and subranges therebewteen, including 2, 5, 10, 20, 25, 30, 40, 50, 60, 75, 85, 90 and 95 wt. %.

The various additives used in preparing the formulations may comprise, e.g., "builders", propylene glycol, optical brightening agents, colorants, etc. These materials and the amounts to be used are well-known to those skilled in the art.

Having generally described this invention, a further understanding can be obtained by reference to certain specific examples which are provided herein for purposes of illustration only and are not intended to be limiting unless otherwise specified.

EXAMPLES

Example 1

The object of this Example is to illustrate the compatibility between various surfactants and a copolymer according to the present invention, where the copolymer has a specific viscosity 0.7.

For each of the Experiments described below, 50 g water, 5 g (dry weight basis) of the polymer being tested, and 10 g (dry weight basis) of the surfactant were added to a 500 mL beaker.

After agitation for several minutes, the resulting composition was set aside for 24 hr.

After 24 hr of being undisturbed, the appearance of the composition was observed.

The composition was rated "unstable" if the mixture had separated into two phases, and was rated "stable" if the mixture appeared to still be a clear solution.

In the latter case, new mixtures were prepared, with increased amounts of surfactant and of the (rheological modifying and/or anti-tartar) polymer, to determine, with the same quantity of water, the point at which the separation of phases occurred.

The amount (dry weight basis) of surfactant and of polymer, added to 50 g water, was then recorded.

The experiments were as follows:

Experiment No.1:
This Experiment illustrates the state of the art. The surfactant was dodecylbenzenesulfonic acid, and the polymer was a sodium polyacrylate with specific viscosity 0.3 (as a rheological modifier, specifically a dispersant).

Experiment No. 2:
This Experiment also illustrates the state of the art. The surfactant was that used in Experiment 1, and the polymer was a sodium polyacrylate with specific viscosity 0.4 (as a dispersant).

Experiment No. 3:
This Experiment also illustrates the state of the art. The surfactant was that used in Experiment 1, and the polymer was a sodium polyacrylate with specific viscosity 0.55 (as a dispersant).

Experiment No. 4:
This Experiment illustrates the invention. The surfactant was that used in Experiment 1, and the polymer was a copolymer with specific viscosity 0.7, having a composition of monomer units as follows:
1. Anionic monomers:
   33 wt. % acrylic acid, and
   3 wt. % methacrylic acid;
2. Cationic Monomers
   21% of methacrylate-type monomer group, where as defined in formula (I)
   $R_6$ is H,
   n =15−m,
   $R_7$ is $CH_3$ $R_8$ is the group —(A)—(O—CH$_2$—CH$_2$)$_m$, in which
m+n=15,
$R_9$ is an alkyl group with 12 carbon atoms,
Z is N, and
X is $SO_4CH_3$,
the structure of this monomer unit is shown below:

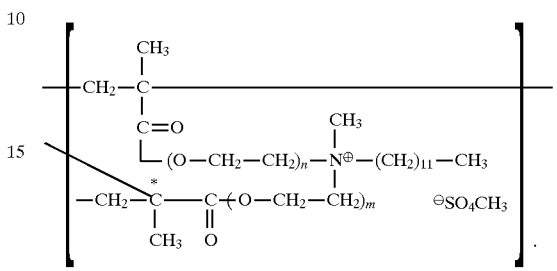

3. Nonionic Monomers:
   43 wt. % acrylamide.

Experiment No. 5:
This Experiment illustrates the state of the art. The surfactant was an isoalkyl sulfate, and the polymer was the sodium polyacrylate used in Experiment 1 (as a dispersant).

Experiment No. 6:
This Experiment also illustrates the state of the art. The surfactant was that used in Experiment 5, and the polymer was the sodium polyacrylate used in Experiment 2 (as a dispersant).

Experiment No. 7:
This Experiment also illustrates the state of the art. The surfactant was that used in Experiment 5, and the polymer was the sodium polyacrylate used in Experiment 3 (as a dispersant).

Experiment No. 8:
This Experiment illustrates the invention. The surfactant was that used in Experiment 5, and the polymer was the copolymer used in Experiment 4.

Experiment No. 9:
This Experiment illustrates the state of the art. The surfactant was a sodium alkyl ether sulfate and the polymer was the sodium polyacrylate used in Experiment 1 (as a dispersant).

Experiment No. 10:
This Experiment also illustrates the state of the art. The surfactant was that used in Experiment 9, and the polymer was the sodium polyacrylate used in Experiment 2 (as a dispersant).

Experiment No. 11:
This Experiment also illustrates the state of the art. The surfactant was that used in Experiment 9, and the polymer was the sodium polyacrylate used in Experiment 3 (as a dispersant).

Experiment No. 12:
This Experiment illustrates the invention. The surfactant was that used in Experiment 9, and the polymer was the copolymer used in Experiment 4.

Experiment No. 13:
This Experiment illustrates the state of the art. The surfactant was an ethoxylated alkylphenol and the polymer was the sodium polyacrylate used in Experiment 1 (as a dispersant).

Experiment No. 14:
This Experiment also illustrates the state of the art. The surfactant was that used in Experiment 13, and the polymer was the sodium polyacrylate used in Experiment 2 (as a dispersant).

Experiment No. 15:

This Experiment also illustrates the state of the art. The surfactant was that used in Experiment 13, and the polymer was the sodium polyacrylate used in Experiment 3 (as a dispersant).

Experiment No. 16:

This Experiment illustrates the invention. The surfactant was that used in Experiment 13, and the polymer was the copolymer used in Experiment 4.

Experiment No. 17:

This Experiment illustrates the state of the art. The surfactant was a polyglycol ether of a fatty alcohol propoxylated 8 times, and the polymer was the sodium polyacrylate used in Experiment 1 (as a dispersant).

Experiment No. 18:

This Experiment also illustrates the state of the art. The surfactant was that used in Experiment 17, and the polymer was the sodium polyacrylate used in Experiment 2 (as a dispersant).

Experiment No. 19:

This Experiment also illustrates the state of the art. The surfactant was that used in Experiment 17, and the polymer was the sodium polyacrylate used in Experiment 3 (as a dispersant).

Experiment No.20:

This Experiment illustrates the invention. The surfactant was that used in Experiment 17, and the polymer was the copolymer used in Experiment 4.

Experiment No.21:

This Experiment illustrates the state of the art. The surfactant was a derivative of an alxylimedazoline, and the polymer was the sodium polyacrylate used in Experiment 1 (as a dispersant).

Experiment No. 22:

This Experiment also illustrates the state of the art. The surfactant was that used in Experiment 21, and the polymer was the sodium polyacrylate used in Experiment 2 (as a dispersant).

Experiment No. 23:

This Experiment also illustrates the state of the art. The surfactant was that used in Experiment 21, and the polymer was the sodium polyacrylate used in Experiment 3 (as a dispersant).

Experiment No. 24:

This Experiment illustrates the invention. The surfactant was that used in Experiment 21, and the polymer was the copolymer used in Experiment 4.

Table 1 summuarizes the amounts of surfactant (grams) at which amounts phase separation was first observed in a mixture comprised of water, the surfactant, and the dispersant polymer. It is clear from Table 1 that, regardless of the charge of the surfactant, the use of a copolymer according to the invention enables higher compatibility to be achieved, which in turn enables the highest possible amounts of surfactant to be tolerated in the mixture without phase separation occurring.

Obviously, additional modifications and variations of the present invention are possible in light of the above teachings. It is therefore to be understood that within the scope of the appended claims, the invention may be practiced otherwise than as specifically described herein.

This Application is based on French Application No. 96 10585, filed Aug. 26, 1996, and incorporated herein by reference in its entirety.

TABLE 1

|  | Experiment No. | Polymer | Specific Viscosity of Polymer | Surfactant | Maximum amount of Polymer Plus Surfactant (grams) Before Phase Separation |
| --- | --- | --- | --- | --- | --- |
| Prior Art | 1 | Sodium Polyacrylate | 0.3 | Dodecylbenzene-sulfonic acid | 15 |
|  | 2 | Sodium Polyacrylate | 0.4 | Dodecylbenzene-sulfonic acid | 15 |
|  | 3 | Sodium Polyacrylate | 0.55 | Dodecylbenzene-sulfonic acid | 15 |
| Invention | 4 | Copolymer used in experiment 4. | 0.7 | Dodecylbenzene-sulfonic acid | 20 |
| Prior Art | 5 | Sodium polyacrylate | 0.3 | Sodium isoalkyl sulfate | 40 |
|  | 6 | Sodium polyacrylate | 0.4 | Sodium isoalkyl sulfate | 35 |
|  | 7 | Sodium polyacrylate | 0.55 | Sodium isoalkyl sulfate | 35 |
| Invention | 8 | Copolymer used in experiment 4 | 0.7 | Sodium isoalkyl sulfate | 40 |
| Prior Art | 9 | Sodium polyacrylate | 0.3 | Alkyl ether sulfate | 25 |
|  | 10 | Sodium polyacrylate | 0.4 | Alkyl ether sulfate | 20 |
|  | 11 | Sodium polyacrylate | 0.55 | Alkyl ether sulfate | 15 |
| Invention | 12 | Copolymer used in Experiment 4. | 0.7 | Alkyl ether sulfate | 40 |
| Prior Art | 13 | Sodium polyacrylate | 0.3 | Ethoxylated alkylphenol | 15 |
|  | 14 | Sodium polyacrylate | 0.4 | Ethoxylated alkylphenol | 15 |
|  | 15 | Sodium polyacrylate | 0.55 | Ethoxylated alkylphenol | 15 |
| Invention | 16 | Copolymer used in Experiment 4. | 0.7 | Ethoxylated alkylphenol | 40 |
| Prior Art | 17 | Sodium polyacrylate | 0.3 | Polyether of a fatty alcohol propoxylated 8 times | 15 |
|  | 18 | Sodium polyacrylate | 0.4 | Polyether of a fatty alcohol propoxylated 8 times | 15 |
|  | 19 | Sodium polyacrylate | 0.55 | Polyether of a fatty alcohol propoxylated 8 times | 15 |
| Invention | 20 | Copolymer used in Experiment 4 | 0.7 | Polyether of a fatty alcohol propoxylated 8 times | 35 |
| Prior Art | 21 | Sodium polyacrylate | 0.3 | Alkylimidazoline derivative | 25 |
|  | 22 | Sodium polyacrylate | 0.4 | Alkylimidazoline derivative | 20 |
|  | 23 | Sodium polyacrylate | 0.55 | Alkylimidazoline derivative | 20 |

TABLE 1-continued

| | Experiment No. | Polymer | Specific Viscosity of Polymer | Surfactant | Maximum amount of Polymer Plus Surfactant (grams) Before Phase Separation |
|---|---|---|---|---|---|
| Invention | 24 | Copolymer used in Experiment 4 | 0.7 | Alkylimidazoline derivative | 40 |

What is claimed as new and desired to be secured by Letters Patent of the United States is:

1. A method of stabilizing a composition comprising at least one surfactant, comprising combining the composition with at least one copolymer comprised of anionic monomer units, cationic monomer units having a surface-active group and, optionally, nonionic monomer units and/or cationic monomer units which do not contain a surface active group, wherein the copolymer is represented by formula (I):

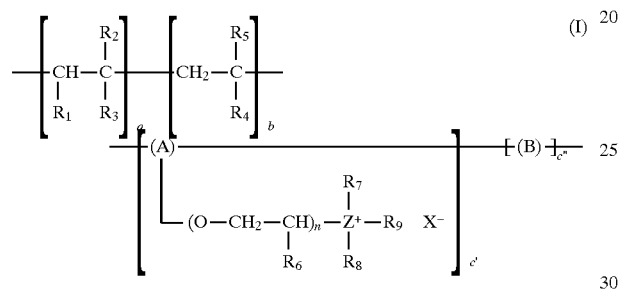

wherein
$R_1$ is H, COOH, or a neutralized COOH group;
$R_2$ is H or $CH_3$;
$R_3$ is a group having at least one acid function, which may be completely or partially neutralized; and
a is the weight percentage of the anionic monomer units, based on the total weight of all monomers, and is 95 to 15 wt. %;
$R_4$ is
—CO—$NH_2$, —CO—$OR_4'$, —CO—$NR_4''R_4'''$, or

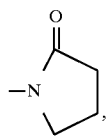

in which
$R_4'$ is an alkyl or alkoxy group having 1 to 4 carbon atoms;
$R_4''$ is H or an alkyl group having 1 to 4 carbon atoms;
$R_4'''$ is an alkyl group having 1 to 4 carbon atoms;
$R_5$ is H or $CH_3$; and
b is the weight percentage of the nonionic monomer units, based on the total weight of all monomers, and is 0 to 65 wt. %;
A is a monomeric unit derived from a polymerizable unsaturated radical selected from the group consisting of acrylate esters, methacrylate esters, maleate esters, maleate hemiesters, itaconate esters, itaconate hemiesters, crotonate esters, vinylphthalate esters, vinylphthalate hemiesters, unsaturated urethanes, allylic ethers, substituted or unsubstituted acrylamides, substituted or unsubstituted methacrylamides and vinyl groups;
$R_6$ is H or $CH_3$;
n is 3 to 30;
$R_7$ is an alkyl group having 1 to 4 carbon atoms;
Z is N or S;
X is a sulfate or halide counterion;
where, when Z is N:
$R_8$ is an alkyl group having 8 to 22 carbon atoms, or a group having the formula

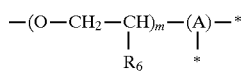

in which
A is as defined above and the two bonds from A indicated by an * are each connected to a monomer unit in another polymer chain of formula (I),
m is 3 to 30, and
$R_6$ is as defined above; and
$R_9$ is an alkyl group having 8 to 22 carbon atoms;
and, when Z is S:
$R_8$ does not exist; and
$R_9$ is an alkyl group having 8 to 22 carbon atoms; and
c' is the weight percentage of the cationic monomer units having a surface-active structure, based on the total weight of all monomers, and is 5 to 60 wt. %;
B is a cationic monomer unit which does not have surface-active structure and is derived from at least one monomer selected from the group consisting of trimethylammoniumethyl acrylate chloride, trimethylammoniumethyl methacrylate chloride, trimethylammoniumethyl acrylate sulfate, trimethylammoniumethyl methacrylate sulfate, N-(N',N',N'-trimethylammonium) propyl acrylamide chloride, N-(N',N',N'-trimethylammonium)propyl methacrylamide chloride, N-(N',N',N'-trimethylammonium)propyl acrylamide sulfate, and N-(N',N',N'-trimethylammonium)propyl methacrylamide sulfate;
c" is the weight percentage of the monomer units having a cationic charge but not having a surface-active structure, based on the total weight of all monomers, and is 0 to 55 wt. %; and
c'+c"=c, where c is the weight percentage of all cationic monomer units, based on the total weight of all monomers, and is 5 to 60 wt. %.

2. The method of claim 1, wherein the surfactant comprises an anionic, cationic, nonionic surfactant, or a mixture thereof.

3. The method of claim 1, wherein the composition is a detergent or cosmetic formulation.

4. The method of claim 1, wherein the composition further comprises water.

5. The method of claim 1, wherein the copolymer has a specific viscosity of 0.3 to 10.

6. The method of claim 1, wherein the copolymer has a specific viscosity of 0.3 to 2.

7. The method of claim 1, wherein the copolymer has a specific viscosity of 0.3 to 1.

8. The method of claim 1, wherein a is 80 to 25 wt. %.

9. The method of claim 1, wherein b is 20 to 50 wt. %.

10. The method of claim 1, wherein c' is 10 to 35 wt. %.

11. The method of claim 1, wherein c" is 1 to 55 wt. %.

12. The method of claim 1, wherein the carboxyl groups in the copolymer are in the form of carboxylic acids.

13. The method of claim 1, wherein at least a portion of the carboxyl groups in the copolymer are neutralized.

14. The method of claim 1, wherein the carboxyl groups in the copolymer are neutralized.

15. A composition comprising at least one surfactant and at least one comprised of anionic monomer units, cationic monomer units having a surface-active group and, optionally, nonionic monomer units and/or cationic monomer units which do not contain a surface active group, wherein the copolymer is represented by formula (I):

$$\left[\begin{array}{c} -CH-C-R_2 \\ | \quad | \\ R_1 \quad R_3 \end{array}\right]_a \left[\begin{array}{c} -CH_2-C-R_5 \\ | \\ R_4 \end{array}\right]_b$$
$$\left[\begin{array}{c} (A) \\ | \\ (O-CH_2-CH)_n-Z^+-R_9 \quad X^- \\ | \quad | \\ R_6 \quad R_8 \end{array}\right]_{c'} [(B)]_{c''}$$

wherein $R_1$ is H, COOH, or a neutralized COOH group;

$R_2$ is H or $CH_3$;

$R_3$ is a group having at least one acid function, which may be completely or partially neutralized; and a is the weight percentage of the anionic monomer units, based on the total weight of all monomers, and is 95 to 15 wt. %;

$R_4$ is
—CO—$NH_2$, —CO—$OR_4'$, —CO—$NR_4"R_4'''$, or $$-N\underset{O}{\bigcirc},$$

in which $R_4'$ is an alkyl or alkoxy group having 1 to 4 carbon atoms;

$R_4"$ is H or an alkyl group having 1 to 4 carbon atoms;

$R_4'''$ is an alkyl group having 1 to 4 carbon atoms;

$R_5$ is H or $CH_3$; and b is the weight percentage of the nonionic monomer units, based on the total weight of all monomers, and is 0 to 65 wt. %;

A is a monomeric unit derived from a polymerizable unsaturated radical selected from the group consisting of acrylate esters, methacrylate esters, maleate esters, maleate hemiesters, itaconate esters, itaconate hemiesters, crotonate esters, vinylphthalate esters, vinylphthalate hemiesters, unsaturated urethanes, allylic ethers, substituted or unsubstituted acrylamides, substituted or unsubstituted methacrylamides and vinyl groups;

$R_6$ is H or $CH_3$;

n is 3 to 30;

$R_7$ is an alkyl group having 1 to 4 carbon atoms;

Z is N or S;

X is a sulfate or halide counterion;

where, when Z is N: p3 $R_8$ is an alkyl group having 8 to 22 carbon atoms, or a group having the formula $$-(O-CH_2-CH)_m-(A)-* \\ \qquad\qquad | \qquad | \\ \qquad\qquad R_6 \qquad *$$

in which

A is as defined above and the two bonds from A indicated by an * are each connected to a monomer unit in another polymer chain of formula (I), m is 3 to 30, and $R_6$ is as defined above; and $R_9$ is an alkyl group having 8 to 22 carbon atoms;

and, when Z is S:

$R_8$ does not exist; and $R_9$ is an alkyl group having 8 to 22 carbon atoms; and c' is the weight percentage of the cationic monomer unit having a surface-active structure, based on the total weight of all monomers, and is 5 to 60 wt. %;

B is a cationic monomer unit which does not have surface-active structure and is derived from at least one monomer selected from the group consisting of trimethylammoniumethyl acrylate chloride, trimethylammoniumethyl methacrylate chloride, trimethylammoniumethyl acrylate sulfate, trimethylammoniumethyl methacrylate sulfate, N-(N',N',N'-trimethylammonium) propyl acrylamide chloride, N-(N',N',N'-trimethylammonium)propyl methacrylamide chloride, N-(N',N',N'-trimethylammonium)propyl acrylamide sulfate, and N-(N',N',N'-trimethylammonium)propyl methacrylamide sulfate;

c" is the weight percentage of the monomer units having a cationic charge but not having a surface-active structure, based on the total weight of all monomers, and is 0 to 55 wt. %; and c'+c"=c, where c is the weight percentage of all cationic monomer units, based on the total weight of all monomers, and is 5 to 60 wt. %.

16. The composition of claim 15, further comprising water.

17. The composition of claim 15, wherein the surfactant comprises an anionic, cationic, nonionic surfactant, or a mixture thereof.

18. The composition of claim 15, wherein the copolymer has a specific viscosity of 0.3 to 10.

19. The composition of claim 15, which is a detergent or cosmetic formulation.

* * * * *

UNITED STATES PATENT AND TRADEMARK OFFICE
CERTIFICATE OF CORRECTION

PATENT NO. : 5,880,085

DATED : March 9, 1999

INVENTOR(S): Yves KENSICHER, et al.

It is certified that an error appears in the above-identified patent and that said Letters Patent is hereby corrected as shown below:

On the Title page, item [45] should be:

--[45] Date of Patent:   *Mar. 9, 1999--

On the Title page, item [*] has been omitted. It should be:

--[*] Notice:   The term of this patent shall not extend beyond the expiration date of Pat. No. 5,783,533.--

Signed and Sealed this

Second Day of May, 2000

*Attest:*

Q. TODD DICKINSON

*Attesting Officer*           *Director of Patents and Trademarks*